United States Patent
Hsu et al.

(10) Patent No.: US 10,325,368 B2
(45) Date of Patent: Jun. 18, 2019

(54) OPTICAL MEASURING APPARATUS AND OPERATING METHOD THEREOF

(71) Applicant: Crystalvue Medical Corporation, Toayuan (TW)

(72) Inventors: Long Hsu, Hsinchu (TW); William Wang, Taoyuan (TW); Cheng-Hsien Liu, Hsinchu (TW); Po-Chen Shih, Kaohsiung (TW); Ting-Sheng Shih, Taichung (TW); Cheng-En Liu, Taipei (TW); Chung-Yu Chou, Taichung (TW); Chung-Cheng Chou, Luzhu Township (TW)

(73) Assignee: Crystalvue Medical Corporation, Taoyuan (TW)

( * ) Notice: Subject to any disclaimer, the term of this patent is extended or adjusted under 35 U.S.C. 154(b) by 169 days.

(21) Appl. No.: 15/498,854

(22) Filed: Apr. 27, 2017

(65) Prior Publication Data

US 2017/0315048 A1    Nov. 2, 2017

Related U.S. Application Data

(60) Provisional application No. 62/483,667, filed on Apr. 10, 2017, provisional application No. 62/328,667, filed on Apr. 28, 2016.

(51) Int. Cl.
*G06T 7/00* (2017.01)
*G01N 15/14* (2006.01)
(Continued)

(52) U.S. Cl.
CPC ....... *G06T 7/0016* (2013.01); *G01N 15/1429* (2013.01); *G01N 15/1436* (2013.01);
(Continued)

(58) Field of Classification Search
CPC ........... G01N 15/1429; G01N 15/1436; G01N 2015/1486; G01N 15/147; G01N 15/1475;
(Continued)

(56) References Cited

U.S. PATENT DOCUMENTS

2006/0202133 A1* 9/2006 Ok ............................ G01J 3/02
250/458.1
2015/0185234 A1* 7/2015 Gibbons ............... B01L 3/0275
506/9
(Continued)

*Primary Examiner* — Anner N Holder
(74) *Attorney, Agent, or Firm* — Patterson + Sheridan, LLP

(57) ABSTRACT

An optical measuring apparatus and an operating method thereof are disclosed. The optical measuring apparatus includes a light source, a carrier chip, a light sensor, an analyzing chip and a display. Samples are uniformly distributed on the carrier chip. The light source emits sensing lights toward the carrier chip. The light sensor receives the sensing lights passing through the carrier chip at a plurality of times to obtain a plurality of images corresponding to the plurality of times respectively. The analyzing chip is coupled to the light sensor. The analyzing chip analyzes the object number and distribution variation with time in the sample according to the plurality of images corresponding to the plurality of times and estimates intrinsic characteristics of the object in the sample accordingly. The display is coupled to the analyzing chip. The display displays the intrinsic characteristics of the object in the sample.

12 Claims, 9 Drawing Sheets

(51) Int. Cl.
*G01N 15/00* (2006.01)
*G01N 15/10* (2006.01)
*G06K 9/00* (2006.01)

(52) U.S. Cl.
CPC . *G06K 9/00134* (2013.01); *G01N 2015/0065* (2013.01); *G01N 2015/1006* (2013.01); *G01N 2015/1486* (2013.01); *G06T 2207/10056* (2013.01); *G06T 2207/30024* (2013.01); *G06T 2207/30242* (2013.01)

(58) Field of Classification Search
CPC ... G01N 2015/0065; G01N 2015/1006; G06K 9/00134; G06K 9/00147; G06T 2207/30242; G06T 7/0016; G06T 2207/10056; G06T 2207/30024; H04N 5/2256
See application file for complete search history.

(56) References Cited

U.S. PATENT DOCUMENTS

2016/0038939 A1\* 2/2016 Min .................... B01L 3/50273
422/506
2016/0225740 A1\* 8/2016 Cheng ................. H01L 25/0753

\* cited by examiner

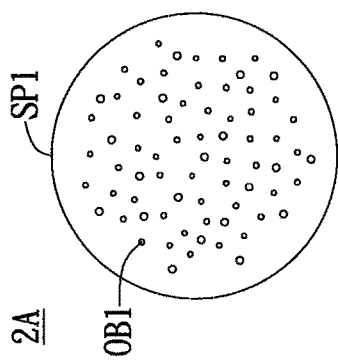
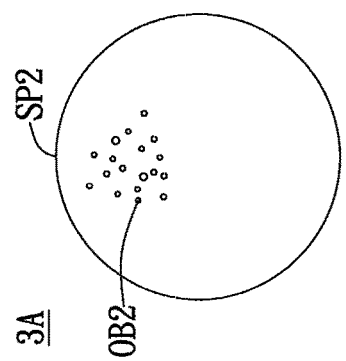
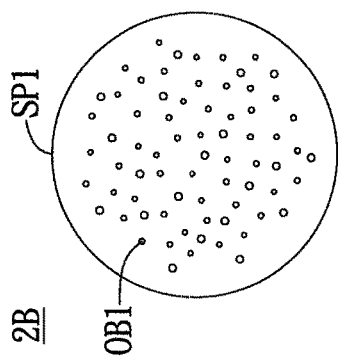
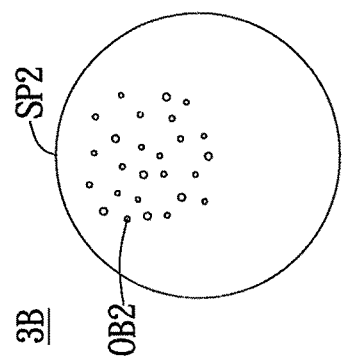
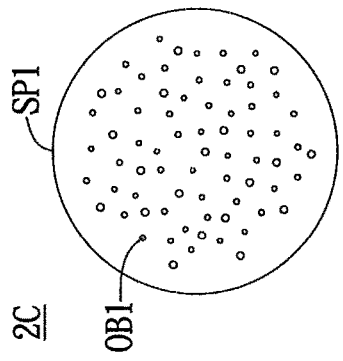
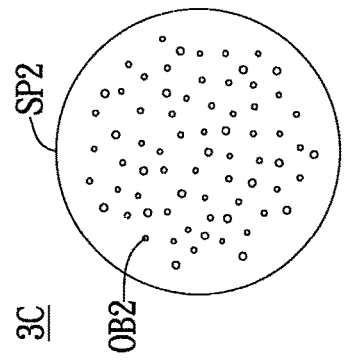
FIG. 2      FIG. 3

OPTICAL MEASURING APPARATUS AND OPERATING METHOD THEREOF

1. REFERENCE TO RELATED APPLICATION

This application claims the benefit of U.S. provisional patent application Ser. No. 62/328,667, filed Apr. 28, 2016 and U.S. provisional patent application Ser. No. 62/483,667, filed Apr. 10, 2017, and the contents of which are hereby incorporated by reference in their entireties.

BACKGROUND OF THE INVENTION

2. Field of the Invention

This invention relates to optical measurement, especially to an optical measuring apparatus and an operating method thereof.

3. Description of the Prior Art

Conventionally, the number of microbiological bodies in biological samples is usually counted in biological experiments; for example, counting the germs, the yeasts or the mold spores. Currently, different methods for counting the number of microbiological bodies are used; for example, microscopic observation and counting method, electronic counter counting method, plate colony counting method, concentration turbidimetric method, cell weight determination method or color changing unit method.

However, in practical applications, the above-mentioned methods for counting the number of microbiological bodies have their own drawbacks or application limitations needed to be overcome and improved.

SUMMARY OF THE INVENTION

Therefore, the invention provides an optical measuring apparatus and an operating method thereof to overcome the problems occurred in the above-mentioned prior arts.

A preferred embodiment of the invention is an optical measuring apparatus. In this embodiment, the optical measuring apparatus includes a light source, a carrier chip, a light sensor, an analyzing chip and a display. Samples are uniformly distributed on the carrier chip. The light source emits sensing lights toward the carrier chip. The light sensor receives the sensing lights passing through the carrier chip at a plurality of times to obtain a plurality of images corresponding to the plurality of times respectively. The analyzing chip is coupled to the light sensor. The analyzing chip analyzes the object number and distribution variation with time in the sample according to the plurality of images corresponding to the plurality of times and estimates intrinsic characteristics of the object in the sample accordingly. The display is coupled to the analyzing chip. The display displays the intrinsic characteristics of the object in the sample.

In an embodiment, the optical measuring apparatus further includes a display. The display is coupled to the analyzing chip and used for displaying the intrinsic characteristics of the object in the sample.

In an embodiment, the carrier chip includes a cover, a plate and a substrate. The cover has at least one injection hole for injecting the object; the plate is disposed under the cover, the plate has a well region corresponding to the at least one injection hole to make the object injected from the at least one injection hole uniformly distributed in the well region; the substrate is disposed under the plate and used for bearing the object.

In an embodiment, the at least one injection hole has a guiding angle for guiding the injection of the object.

In an embodiment, an area of the well region is larger than an area of the injection hole, and the injection hole corresponds to a position in the well region.

In an embodiment, the optical measuring apparatus further includes a cleaning unit disposed under the carrier chip, when the carrier chip moves to a position above the light sensor, the cleaning unit contacts with a surface of the light sensor and cleans the surface of the light sensor.

In an embodiment, the optical measuring apparatus further includes a cassette disposed above the light sensor and adjacent to the light sensor, the cassette is used for accommodating the carrier chip.

Another embodiment of the invention is an optical measuring apparatus operating method for operating an optical measuring apparatus. The optical measuring apparatus includes a light source, a carrier chip, a light sensor and an analyzing chip. The analyzing chip couples to the light sensor.

The optical measuring apparatus operating method includes steps of: uniformly distributing a sample on the carrier chip; the light source emitting a sensing light toward the carrier chip; the light sensor receiving the sensing light passing through the carrier chip at a plurality of times to obtain a plurality of images corresponding to the plurality of times respectively; and the analyzing chip analyzing an object number variation with time and a object distribution variation with time in the sample according to the plurality of images corresponding to the plurality of times and estimating intrinsic characteristics of the object in the sample accordingly.

Compared to the prior art, the optical measuring apparatus and the operating method thereof in the invention can effectively improve the drawbacks of the optical measuring apparatus in the prior arts. The optical measuring apparatus and the operating method thereof in the invention can not only accurately count the number of objects in a sample, but also the estimate intrinsic characteristics of objects in the sample accordingly. Therefore, the optical measuring apparatus and the operating method thereof in the invention can be widely used in the detections of various microorganisms or environment.

The advantage and spirit of the invention may be understood by the following detailed descriptions together with the appended drawings.

BRIEF DESCRIPTION OF THE APPENDED DRAWINGS

FIG. 2 illustrates schematic diagrams of the first image 2A, the second image 2B and the third image 2C of the first sample SP1 obtained at the first time, the second time and the third time respectively.

FIG. 3 illustrates schematic diagrams of the first image 3A, the second image 3B and the third image 3C of the second sample SP2 obtained at the first time, the second time and the third time respectively.

Figure 4A:
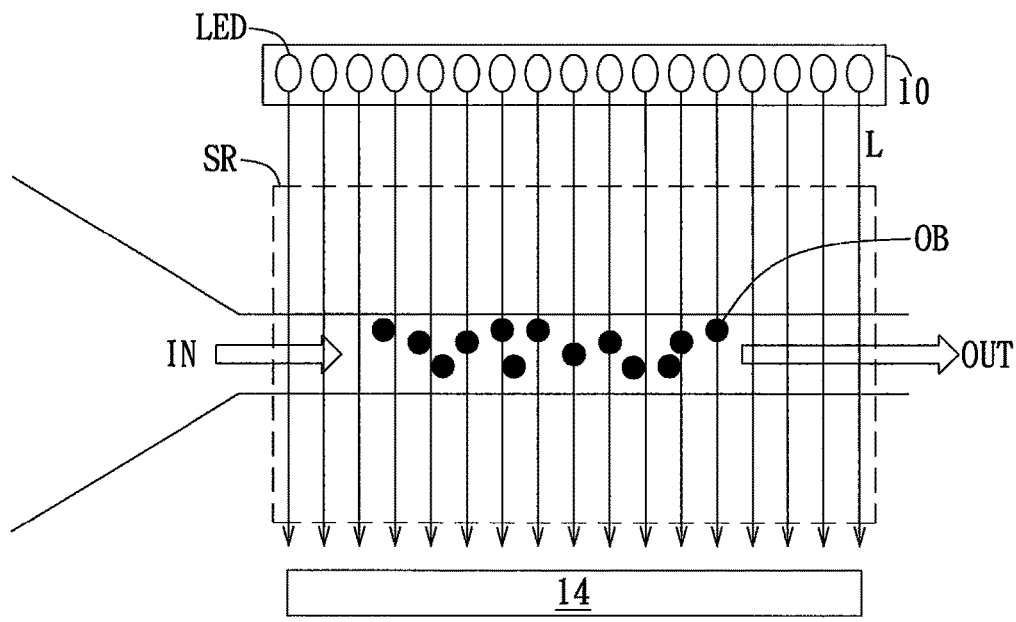
Figure 4B:
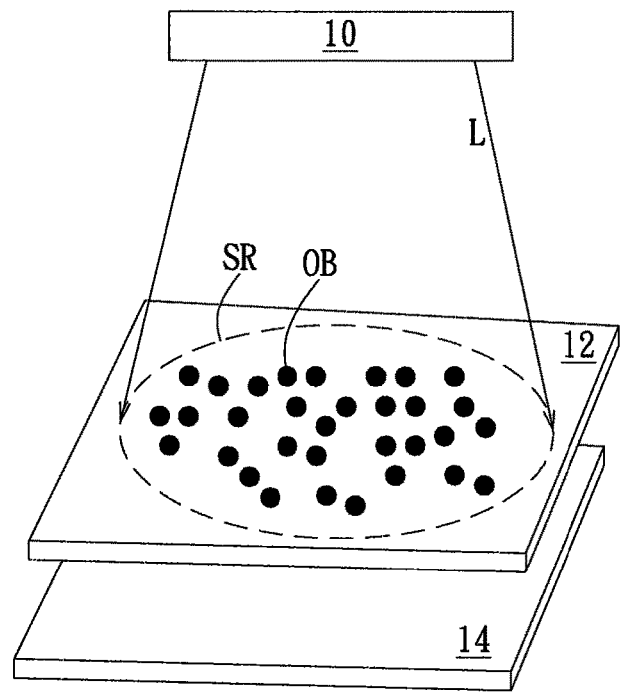
Figure 4C:
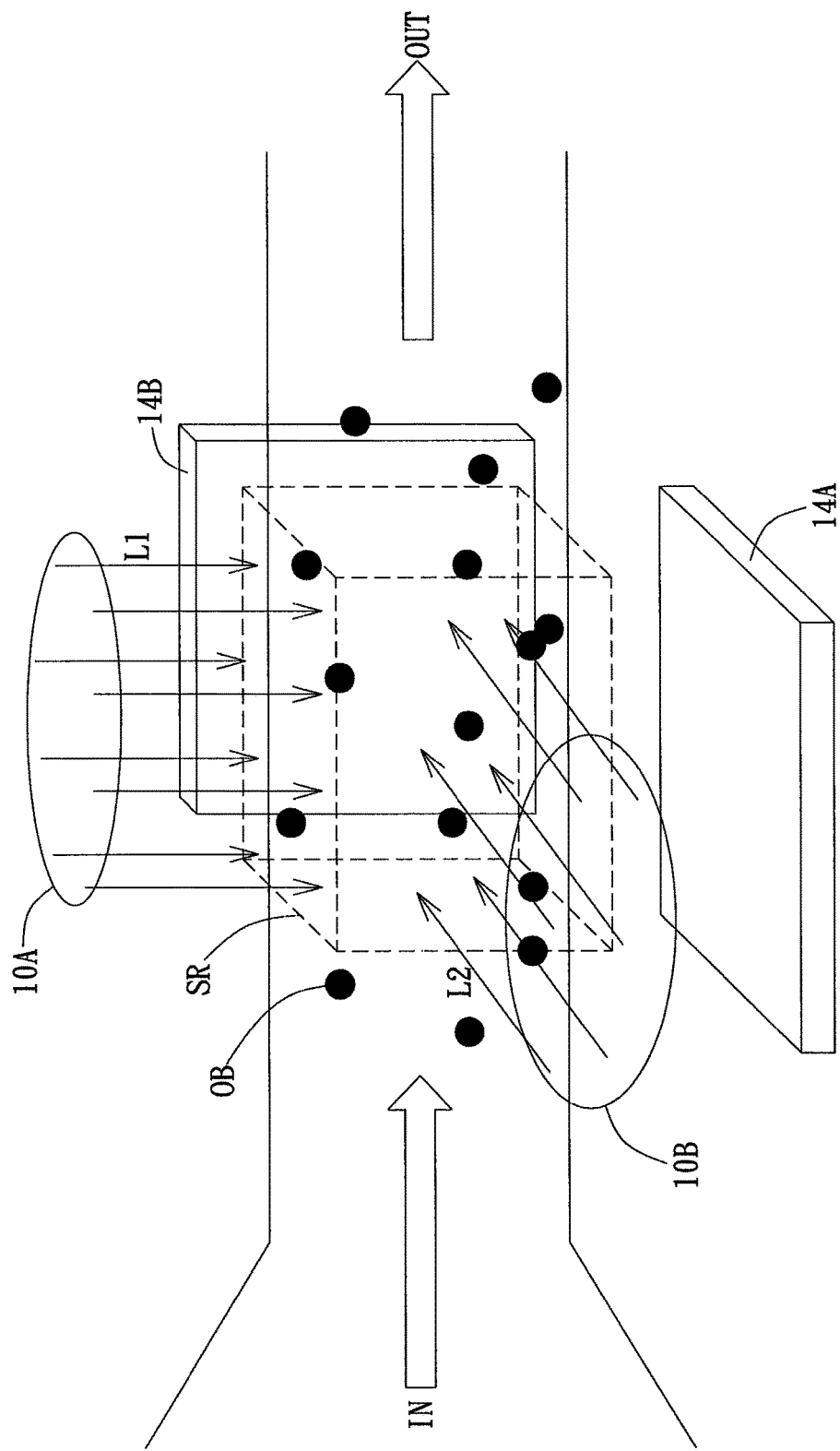

FIG. 4A~FIG. 4C illustrate schematic diagrams of performing 1-D optical sensing, 2-D optical sensing and 3-D optical sensing on the object OB respectively.

Figure 5A:
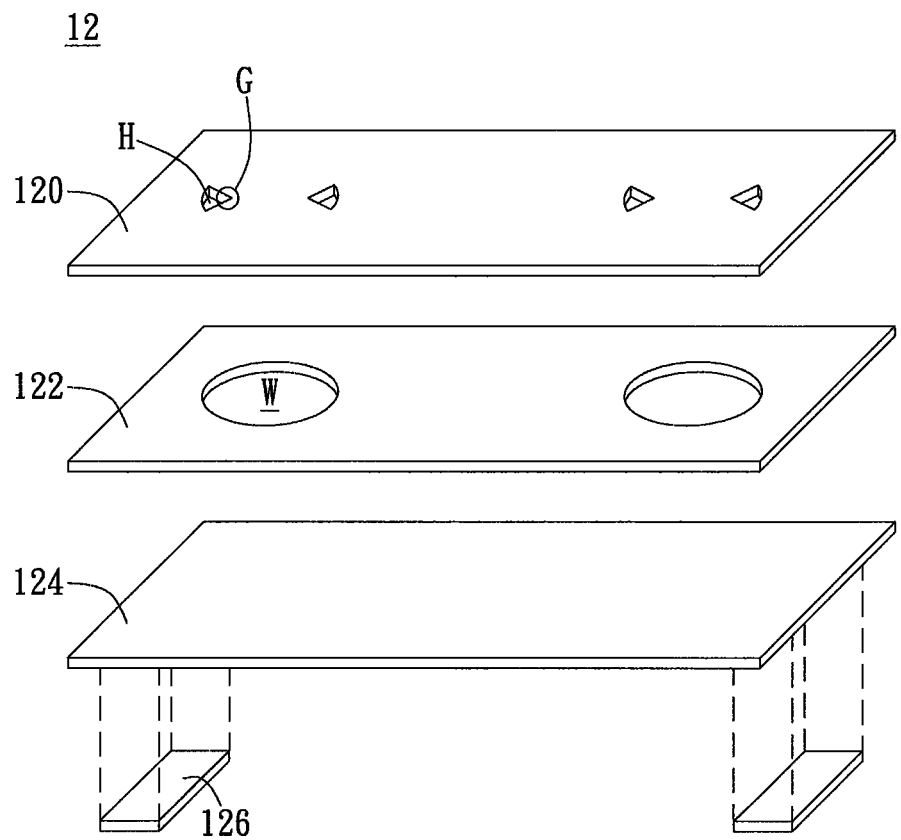
Figure 5B:
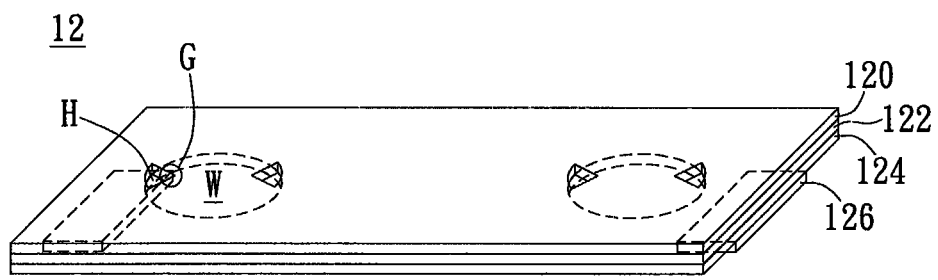

FIG. 5A~FIG. 5B illustrate an exploded diagram and a schematic diagram of the carrier chip 12 respectively.

Figure 6:
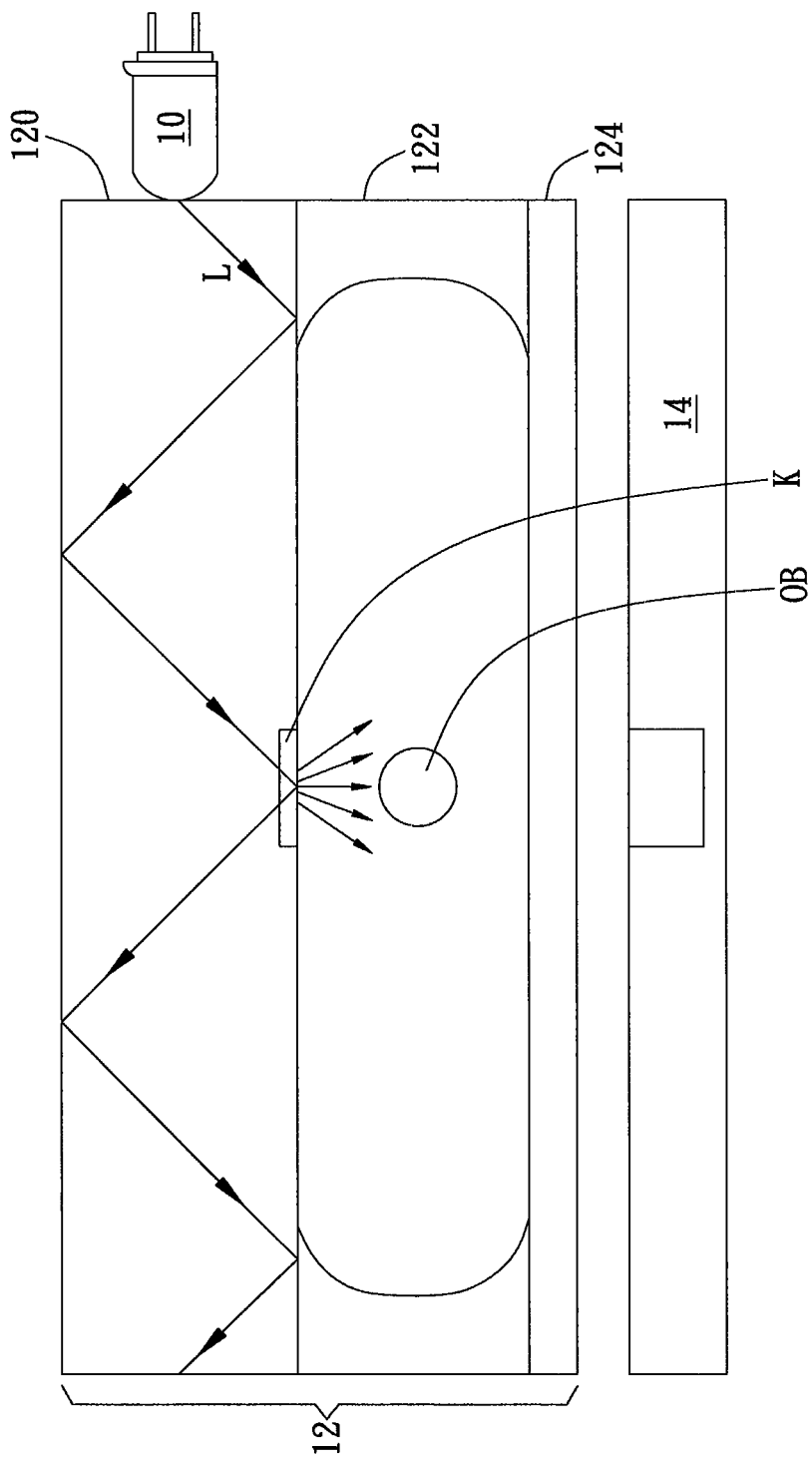

FIG. 6 illustrates an embodiment that the light source 10 is a lateral light source.

Figure 7:
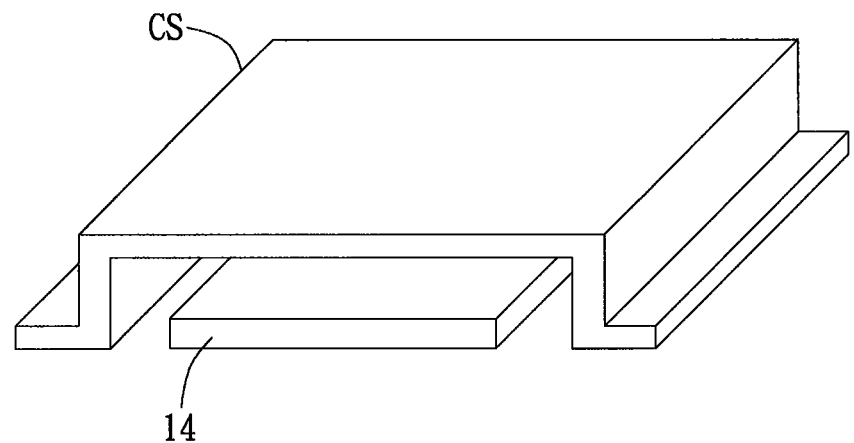

FIG. 7 illustrates an embodiment of the optical measuring apparatus including a cassette CS.

FIG. 8A~FIG. 8D illustrate different embodiments of the optical measuring apparatus 1 further including a switching unit SW respectively.

Figure 9:
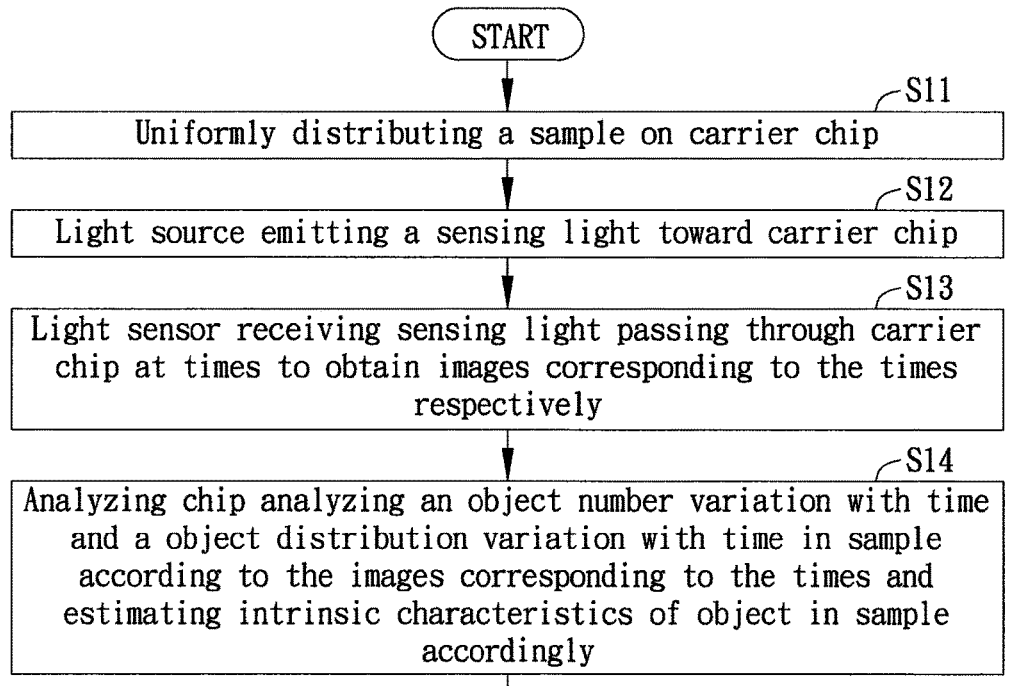

FIG. 9 illustrates a flowchart of the optical measuring apparatus operating method in another embodiment of the invention.

DETAILED DESCRIPTION OF THE INVENTION

A preferred embodiment of the invention is an optical measuring apparatus. In this embodiment, the optical measuring apparatus can detect the number and distribution of the objects (e.g., biological cells or other microorganisms) in biological samples and further estimate intrinsic characteristics of the objects in the biological samples accordingly, but not limited to this. It can be widely used in different application areas, such as the bacteria number detection in food or water samples, the bacteria number detection in the water of (fish, shrimp or crab) farms, the suspended particle detection in air, environmental UV detection, water quality testing, human disease (roundworm or pinworm) detection, plant pathogen detection, antigen or antibody detection, or instant record of cell growth status.

Figure 1:
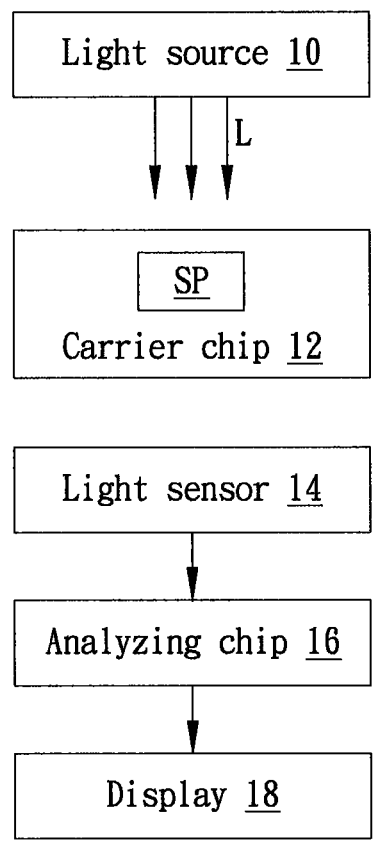
FIG. 1 illustrates a functional block diagram of the optical measuring apparatus in a preferred embodiment of the invention.

Please refer to FIG. 1. FIG. 1 illustrates a functional block diagram of the optical measuring apparatus in this embodiment. As shown in FIG. 1, the optical measuring apparatus 1 includes a light source 10, a carrier chip 12, a light sensor 14, an analyzing chip 16 and a display 18. Wherein, the analyzing chip 16 is coupled to the light sensor 14; the display 18 is coupled to the analyzing chip 16.

The light source 10 emits the sensing lights L toward the samples SP disposed on the carrier chip 12. The samples SP are uniformly distributed on the carrier chip 12. When the sensing lights L from the light source 10 are emitted to the samples SP on the carrier chip 12, the sensing lights L may be refracted, scattered or absorbed by the samples SP; the samples SP may be self-luminous. Therefore, the light sensor can receive the sensing lights L passing through the carrier chip 12 at different times respectively to obtain a plurality of images corresponding to the different times respectively.

Then, the analyzing chip 16 will analyze the object number variation and object distribution variation with time in the sample SP according to the images corresponding to the different times. Afterward, the analyzing chip 16 will estimate intrinsic characteristics of the objects in the sample SP accordingly. At last, the display 18 will display the intrinsic characteristics of the objects in the sample SP.

In an embodiment, as shown in FIG. 2, it is assumed that the light sensor 14 obtains the first image 2A, the second image 2B and the third image 2C of the first sample SP1 corresponding to the first time, the second time and the third time respectively. It can be found that the number and the distribution of the first objects OB1 in the first sample SP1 in the first image 2A, the second image 2B and the third image 2C are approximately the same; that is to say, from the first time to the third time, the number and the distribution of the first objects OB1 in the first sample SP1 have very small variation with time and can be almost negligible. Therefore, the analyzing chip 16 can estimate that the activity of the first objects OB1 in the first sample SP1 is very small, even most of the first objects OB1 in the first sample SP1 may have died, and the display 18 will display this estimated intrinsic characteristics of the objects in the first sample SP1 for the user reference.

In another embodiment, as shown in FIG. 3, it is assumed that the light sensor 14 obtains the first image 3A, the second image 3B and the third image 3C of the second sample SP2 corresponding to the first time, the second time and the third time respectively. It can be found that the number and the distribution of the second objects OB2 in the second sample SP2 in the first image 3A, the second image 3B and the third image 3C are obviously different; that is to say, from the first time to the third time, the number and the distribution of the second objects OB2 in the second sample SP2 have very large variation with time. Therefore, the analyzing chip 16 can estimate that most of the second objects OB2 in the second sample SP2 may be still alive and the number of the second objects OB2 in the second sample SP2 is increasing, and the display 18 will display this estimated intrinsic characteristics of the objects in the second sample SP2 for the user reference.

In practical applications, the light source 10 can be a visible light source emitting visible lights or a non-visible light source emitting non-visible lights such as UV lights; the light source 10 can be designed as a single light source or a matrix-type light source and can be controlled to only let small-angle sensing light L emitted into the light sensor 14, but not limited to this. The carrier chip 12 can be 1-D sensing type, 2-D sensing type or 3-D sensing type based on practical needs. Functionally, the carrier chip 12 can only provide object carrying function or can be a functional carrier chip additionally providing other functions; for example, the carrier chip 12 can be pre-designed to include reactants having different colors, sizes or shapes or reacted to different samples and the products or the remaining reactants after the reaction between the reactants and the samples can be calculated, but not limited to this. The samples SP can be fluid including object particles, but not limited to this.

In practical applications, the light sensor 14 can be a charge-coupled device (CCD) image sensor or a complementary metal-oxide-semiconductor (CMOS) image sensor; in order to cooperated with the carrier chip 12 having 1-D sensing type, 2-D sensing type or 3-D sensing type, the light sensor 14 can be 1-D line-type light sensor or 2-D plane-type light sensor, but not limited to this. For example, FIG. 4A~FIG. 4C illustrate schematic diagrams of performing 1-D optical sensing, 2-D optical sensing and 3-D optical sensing on the object OB respectively. As shown in FIG. 4A, the line-type light source 10 and the line-type light sensor 14 are used; as shown in FIG. 4B, the plane-type light source 10 and the plane-type light sensor 14 are used; as shown in FIG. 4C, two plane-type light sources 10A and 10B and two plane-type light sensors 14A and 14B are used.

The analyzing chip 16 can select a suitable algorithm to analyze the number of the objects in the image based on practical needs, but not limited to this. The display 18 can be a counting display only displaying the number of the objects or a multi-functional display including an interactive panel which can display the content including the captured image and the number of the objects by selecting different system detection modes cooperated with corresponding chip designs or the display 18 can use a dynamical refreshing display mode or a static displaying mode based on practical needs, but not limited to this. The intrinsic characteristics of the objects in the sample can be not only the life and death or activity of the objects, but also the color, temperature or humidity of the objects; if the objects are self-luminous, the intrinsic characteristics of the objects can be also the lightness of the objects, but not limited to this.

It should be noticed that if the carrier chip 12 is a functional carrier chip, it can have different applications such as:

(1) Detecting bacteria or antigen: the carrier chip 12 has multiple inlet flow passages for the antibody or bacterial test agent fully mixed with the antigen or bacteria, and then the optical tweezer is used to generate grasping force to drive particles having different sizes, and the number of the bacteria or antigen in the image will be counted.

(2) Detecting autologous illuminant: the carrier chip 12 is designed to have multiple chip base blocks having different light transmittances (e.g., each block includes particles having different light transmittances) and the objects are uniformly distributed on the carrier chip 12. By doing so, if the objects are autologous illuminant, the lightness of the objects can be obtained by detecting the number of the particles in the image.

(3) Performing environmental detection: after the reaction between the external environment and the reactants in the carrier chip 12, the product will be generated accordingly, and the condition of the external environment can be estimated by detecting the number of the product particles.

Then, the structure of the carrier chip 12 will be introduced in detail. Please refer to FIG. 5A and FIG. 5B. FIG. 5A~FIG. 5B illustrate an exploded diagram and a schematic diagram of the carrier chip 12 respectively. As shown in FIG. 5A and FIG. 5B, the carrier chip 12 can include a cover 120, a plate 122 and a substrate 124. The cover 120 has at least one injection hole H for injecting the object. The plate 122 is disposed under the cover 120, and the plate 122 has a well region W corresponding to the injection hole H to make the object injected from the injection hole H uniformly distributed in the well region W. The substrate 124 is disposed under the plate 122 and used for bearing the object. In fact, an area of the well region W will be larger than an area of the injection hole H, and the injection hole H corresponds to a position in the well region W. The shape of the well region W can be ellipse, circle or other shapes. For example, if the shape of the well region W is circle, the position of the injection hole H can correspond to any positions in the well region W, such as circumferential edge or the center of the circle.

It should be noticed that the injection hole H on the cover 120 has a guiding angle G for guiding the injection of the objects, so that the objects can be injected into the well region W smoothly and distributed in the well region W uniformly. The shape of the injection hole H on the cover 120 can be triangle or other shapes having the guiding angle G, but not limited to this.

In addition, as shown in FIG. 5A and FIG. 5B, a cleaning unit 126 can be disposed under the substrate 124 of the carrier chip 12. When the carrier chip 12 moves to a position above the light sensor 14 (e.g., the CCD image sensor), since the substrate 124 of the carrier chip 12 is adjacent to the light sensor 14, the cleaning unit 126 disposed under the substrate 124 will contact with a surface of the light sensor 14 (e.g., the surface of the CCD image sensor) to clean the surface of the light sensor 14. In fact, the cleaning unit 126 can be a cotton sheet which is moistened with alcohol, but not limited to this.

It should be noticed that the carrier chip 12 in the above-mentioned embodiments has a three-tier structure; in practical applications, the carrier chip 12 can have other structures. For example, the carrier chip 12 can have a double-layer structure only including the cover 120 and the substrate 124, wherein the substrate 124 is dug a groove as the well region W and then the substrate 124 is bonded with the cover 120, but not limited to this.

In an embodiment, as shown in FIG. 6, the light source 10 can be used as a lateral light source disposed at a side of the cover 120 of the carrier chip 12. The sensing light L from the light source 10 is emitted into the cover 120 and then reflected by the inner wall of the cover 120 toward another side of the cover 120. When the reflected sensing light L is emitted to the grid unit K in the cover 120, the sensing light L will be refracted or scattered to the object OB in the plate 122 by the grid unit K.

In practical applications, the optical measuring apparatus 1 can include a housing (not shown in the figures) which can provides different functions such as water-proof, dust-proof, shock-proof, drop-proof, scratch-proof and anti-ultraviolet light; the optical measuring apparatus 1 can be designed as a desktop-type device or a portable device which can be connected to computer, smart phone or cloud database, but not limited to this.

Figure 8A:
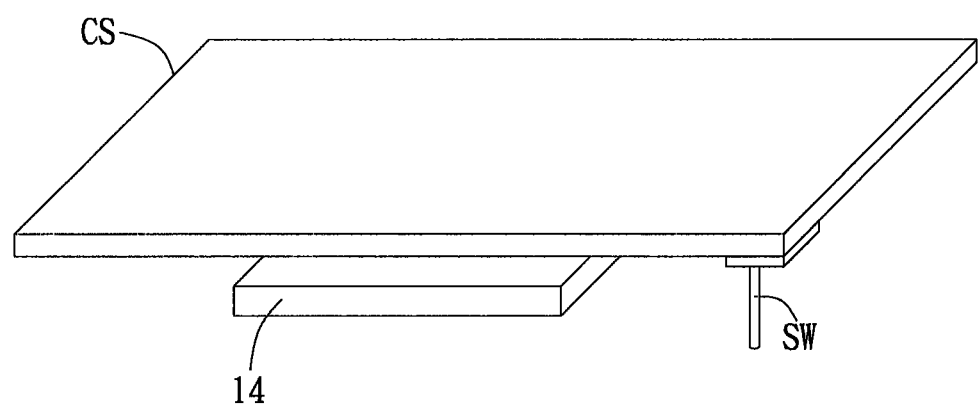

In addition, as shown in FIG. 7 and FIG. 8A, the optical measuring apparatus 1 can include a cassette CS. The cassette CS is disposed above the light sensor 14 (e.g., the CCD image sensor) and near the light sensor 14 to accommodate the carrier chip 12. An engaging unit (not shown in the figures) can be disposed in the cassette to engage the carrier chip 12 to a specific location to facilitate the subsequent measurements.

As shown in FIG. 8A, in an embodiment, the optical measuring apparatus 1 further includes a switching unit SW. When the cassette CS moves to the specific location and contacts with the switching unit SW, the switching unit SW will be switched on to start the optical measuring function of the optical measuring apparatus 1.

Figure 8B:
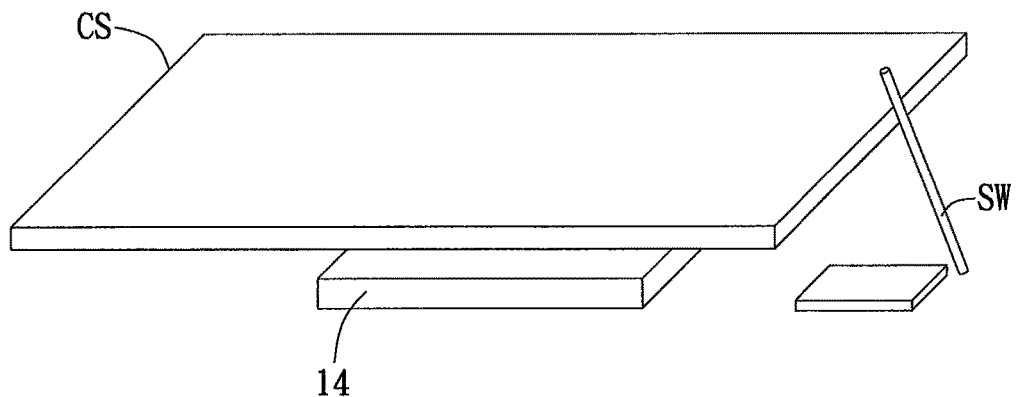
Figure 8C:
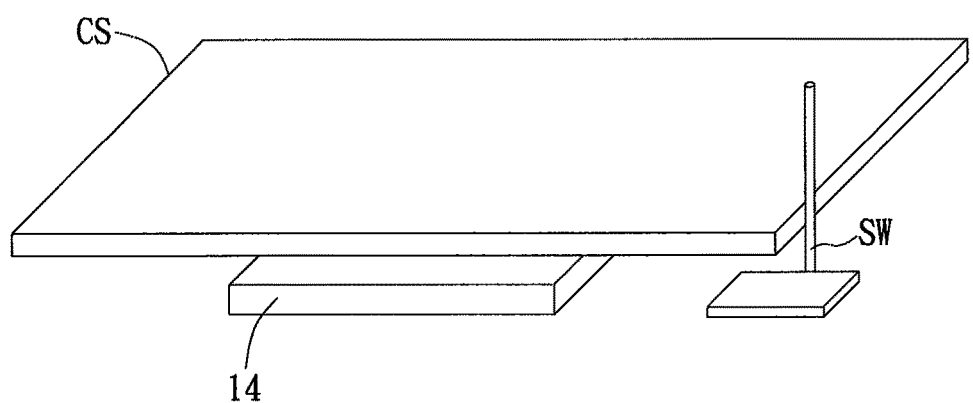

As shown in FIG. 8B, in another embodiment, when the cassette CS does not move to the specific location yet, the switching unit SW will not contact with the cassette CS, so that the switching unit SW is still switched off, and the optical measuring function of the optical measuring apparatus 1 will not be started; as shown in FIG. 8C, when the cassette CS moves to the specific location and contacts with the switching unit SW, the switching unit SW will be switched on to start the optical measuring function of the optical measuring apparatus 1.

Figure 8D:
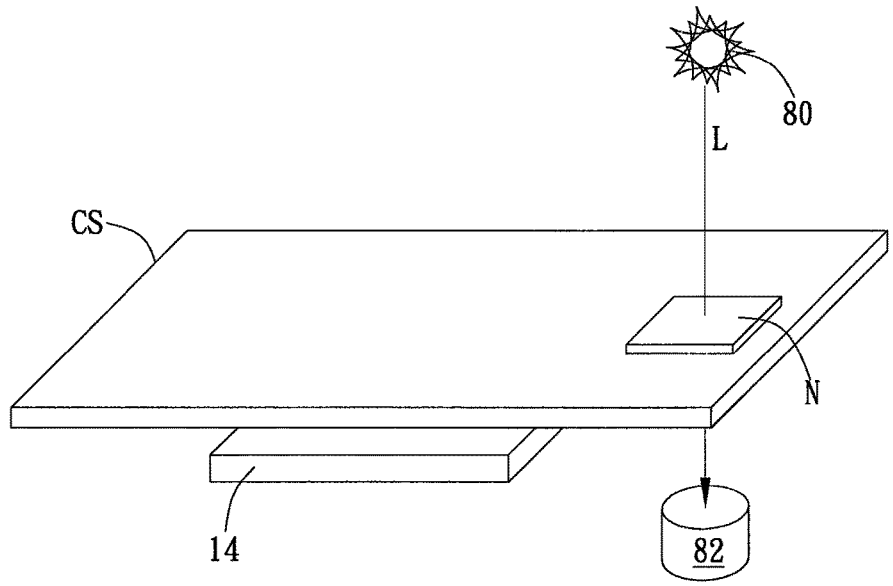

As shown in FIG. 8D, in another embodiment, when the cassette CS moves to the specific location, the light L from the light source 80 can be emitted through the hole N into the switching unit 82, and the switching unit SW will be switched on to start the optical measuring function of the optical measuring apparatus 1.

In practical applications, in order to avoid distorted counting results due to the overlapping of objects in the sample SP, the optical measuring apparatus 1 can also include a vibration module (not shown in the figures) used to vibrate the cassette accommodating the carrier 12 before the optical measuring apparatus 1 starts its optical measurement, so that the overlapped objects in the sample SP of the carrier chip 12 can be separated to obtain more accurate counting results.

In addition, in order to avoid the uneven distribution of the objects in the sample SP of the carrier chip 12, not only the guiding angle G of the injection hole H on the cover 120 can guide the objects to be uniformly distributed in the well region W, but also the vibration module (not shown in the figures) can vibrate at a specific vibration frequency to make the distribution of the objects in the well region W become more uniform to obtain more accurate counting results.

Another embodiment of the invention is an optical measuring apparatus operating method. In this embodiment, the optical measuring apparatus operating method is used for operating an optical measuring apparatus. The optical measuring apparatus includes a light source, a carrier chip, a light sensor and an analyzing chip. The analyzing chip couples to the light sensor.

Please refer to FIG. 9. FIG. 9 illustrates a flowchart of the optical measuring apparatus operating method in this embodiment. As shown in FIG. 9, the optical measuring apparatus operating method includes steps of:

Step S11: uniformly distributing a sample on the carrier chip;

Step S12: the light source emitting a sensing light toward the carrier chip;

Step S13: the light sensor receiving the sensing light passing through the carrier chip at a plurality of times to obtain a plurality of images corresponding to the plurality of times respectively; and Step S14: the analyzing chip analyzing an object number variation with time and a object distribution variation with time in the sample according to the plurality of images corresponding to the plurality of times and estimating intrinsic characteristics of the object in the sample accordingly. As to the detail of the operation of the optical measuring apparatus, it can be found in the above-mentioned embodiments and not repeated in this.

Compared to the prior art, the optical measuring apparatus and the operating method thereof in the invention can effectively improve the drawbacks of the optical measuring apparatus in the prior arts. The optical measuring apparatus and the operating method thereof in the invention can not only accurately count the number of objects in a sample, but also the estimate intrinsic characteristics of objects in the sample accordingly. Therefore, the optical measuring apparatus and the operating method thereof in the invention can be widely used in the detections of various microorganisms or environment.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical measuring apparatus, comprising:
   a carrier chip, wherein a sample is uniformly distributed on the carrier chip;
   a light source for emitting a sensing light toward the carrier chip;
   a light sensor for receiving the sensing light passing through the carrier chip at a plurality of times to obtain a plurality of images corresponding to the plurality of times respectively;
   an analyzing chip, coupled to the light sensor, for analyzing an object number variation with time and an object distribution variation with time in the sample according to the plurality of images corresponding to the plurality of times and estimating intrinsic characteristics of the object in the sample accordingly; and
   a cleaning unit disposed under the carrier chip, when the carrier chip moves to a position above the light sensor, the cleaning unit contacting with a surface of the light sensor and cleaning the surface of the light sensor.

2. The optical measuring apparatus of claim 1, further comprising:
   a display, coupled to the analyzing chip, for displaying the intrinsic characteristics of the object in the sample.

3. The optical measuring apparatus of claim 1, wherein the carrier chip comprises:
   a cover having at least one injection hole for injecting the object;
   a plate disposed under the cover, the plate having a well region corresponding to the at least one injection hole to make the object injected from the at least one injection hole uniformly distributed in the well region; and
   a substrate, disposed under the plate, for bearing the object.

4. The optical measuring apparatus of claim 3, wherein the at least one injection hole has a guiding angle for guiding the injection of the object.

5. The optical measuring apparatus of claim 3, wherein an area of the well region is larger than an area of the injection hole, and the injection hole corresponds to a position in the well region.

6. An optical measuring apparatus, comprising:
   a carrier chip, wherein a sample is uniformly distributed on the carrier chip;
   a light source for emitting a sensing light toward the carrier chip;
   a light sensor for receiving the sensing light passing through the carrier chip at a plurality of times to obtain a plurality of images corresponding to the plurality of times respectively;
   an analyzing chip, coupled to the light sensor, for analyzing an object number variation with time and an object distribution variation with time in the sample according to the plurality of images corresponding to the plurality of times and estimating intrinsic characteristics of the object in the sample accordingly; and
   a cassette, disposed above the light sensor and adjacent to the light sensor, for accommodating the carrier chip.

7. An optical measuring apparatus operating method for operating an optical measuring apparatus, the optical measuring apparatus comprising a light source, a carrier chip, a light sensor and an analyzing chip, the analyzing chip coupling to the light sensor, the optical measuring apparatus operating method comprising steps of:
   uniformly distributing a sample on the carrier chip;
   the light source emitting a sensing light toward the carrier chip;
   the light sensor receiving the sensing light passing through the carrier chip at a plurality of times to obtain a plurality of images corresponding to the plurality of times respectively; and
   the analyzing chip analyzing an object number variation with time and a object distribution variation with time in the sample according to the plurality of images corresponding to the plurality of times and estimating intrinsic characteristics of the object in the sample accordingly;
   wherein the optical measuring apparatus further comprises a cleaning unit disposed under the carrier chip, when the carrier chip moves to a position above the light sensor, the cleaning unit contacts with a surface of the light sensor and cleans the surface of the light sensor.

8. The optical measuring apparatus operating method of claim 7, wherein the optical measuring apparatus further comprises a display, the display is coupled to the analyzing chip and used for displaying the intrinsic characteristics of the object in the sample.

9. The optical measuring apparatus operating method of claim 7, wherein the carrier chip comprises a cover, a plate and a substrate, the cover has at least one injection hole for injecting the object; the plate is disposed under the cover, the plate has a well region corresponding to the at least one injection hole to make the object injected from the at least one injection hole uniformly distributed in the well region; the substrate is disposed under the plate and used for bearing the object.

10. The optical measuring apparatus operating method of claim 9, wherein the at least one injection hole has a guiding angle for guiding the injection of the object.

11. The optical measuring apparatus operating method of claim 9, wherein an area of the well region is larger than an area of the injection hole, and the injection hole corresponds to a position in the well region.

12. The optical measuring apparatus operating method of claim 7, wherein the optical measuring apparatus further comprises a cassette disposed above the light sensor and adjacent to the light sensor, the cassette is used for accommodating the carrier chip.

* * * * *